US010568713B2

(12) United States Patent
Kruger et al.

(10) Patent No.: US 10,568,713 B2
(45) Date of Patent: Feb. 25, 2020

(54) NAVIGATION ASSISTANCE SYSTEM FOR MEDICAL INSTRUMENTS

(71) Applicant: Fiagon AG Medical Technologies, Hennigsdorf (DE)

(72) Inventors: Timo Kruger, Berlin (DE); Dirk Mucha, Berlin (DE)

(73) Assignee: Fiagon AG Medical Technologies, Henningsdorf (DE)

( * ) Notice: Subject to any disclaimer, the term of this patent is extended or adjusted under 35 U.S.C. 154(b) by 34 days.

(21) Appl. No.: 15/303,793

(22) PCT Filed: Apr. 14, 2015

(86) PCT No.: PCT/EP2015/058107
§ 371 (c)(1),
(2) Date: Nov. 7, 2016

(87) PCT Pub. No.: WO2015/158736
PCT Pub. Date: Oct. 22, 2015

(65) Prior Publication Data
US 2017/0105809 A1 Apr. 20, 2017

(30) Foreign Application Priority Data
Apr. 15, 2014 (DE) .................. 10 2014 207 274

(51) Int. Cl.
*A61B 34/20* (2016.01)
*G06T 11/60* (2006.01)
(Continued)

(52) U.S. Cl.
CPC .......... *A61B 90/37* (2016.02); *A61B 1/00009* (2013.01); *A61B 1/00045* (2013.01);
(Continued)

(58) Field of Classification Search
CPC .... A61B 90/37; A61B 34/20; H04N 5/23293; G06T 7/0012; G06T 2207/10068; G06T 2207/10072
(Continued)

(56) References Cited

U.S. PATENT DOCUMENTS

| 6,248,074 B1* | 6/2001 | Ohno ....................... A61B 8/12 128/916 |
| 6,370,420 B1* | 4/2002 | Kraft ...................... A61B 5/032 348/77 |
| 6,661,571 B1 | 12/2003 | Shioda et al. |
| 6,690,960 B2* | 2/2004 | Chen ...................... A61B 90/36 348/77 |
| 7,474,327 B2* | 1/2009 | Davidson ........... A61B 1/00045 348/77 |

(Continued)

FOREIGN PATENT DOCUMENTS

| EP | 1080695 A1 | 3/2001 |
| JP | 2011 036600 A | 2/2011 |
| WO | 2005/039391 A2 | 5/2005 |

*Primary Examiner* — Thai Q Tran
*Assistant Examiner* — Jose M Mesa
(74) *Attorney, Agent, or Firm* — Ware, Fressola, Maguire & Barber LLP

(57) ABSTRACT

A navigation support system for medical instruments comprises a signal processing unit with an input for real-time video image signals from an optical instrument, input for instrument position signals and access to tomography image data, and output for outputting image signals. The signal processing unit generates output image signals from the image signals, the image data and the position signals and generates the output image signals such that the real-time video image signals are displayed permanently centrally on an image display unit connected to the navigation support system in a round or oval central image display of an overall image, wherein the central image display extends at least in one direction of extension across more than half of the overall image and that the secondary images generated by tomography image data, in dependence on the instrument position signals, are displayed adjacent to or partially superimposed over the central image display.

12 Claims, 8 Drawing Sheets

(51) Int. Cl.
*A61B 90/00* (2016.01)
*A61B 34/00* (2016.01)
*A61B 1/00* (2006.01)
*G06T 7/00* (2017.01)
*H04N 5/232* (2006.01)
*H04N 5/225* (2006.01)

(52) U.S. Cl.
CPC .............. *A61B 34/20* (2016.02); *A61B 34/25* (2016.02); *A61B 90/36* (2016.02); *G06T 7/0012* (2013.01); *G06T 11/60* (2013.01); *H04N 5/23293* (2013.01); *G06T 2207/10016* (2013.01); *G06T 2207/10068* (2013.01); *G06T 2207/10072* (2013.01); *G06T 2207/30004* (2013.01); *G06T 2207/30196* (2013.01); *H04N 2005/2255* (2013.01)

(58) Field of Classification Search
USPC .......................................................... 348/77
See application file for complete search history.

(56) References Cited

U.S. PATENT DOCUMENTS

| | | | |
|---|---|---|---|
| 2005/0054895 | A1 | 3/2005 | Hoeg et al. |
| 2005/0085717 | A1 | 4/2005 | Shahidi |
| 2006/0033679 | A1* | 2/2006 | Gunji .................... G06T 11/008 345/33 |
| 2007/0167754 | A1* | 7/2007 | Okuno ................. A61B 1/0005 600/437 |
| 2009/0192519 | A1 | 7/2009 | Omori |
| 2010/0220914 | A1* | 9/2010 | Iwase .................. A61B 5/0066 382/131 |
| 2010/0229118 | A1* | 9/2010 | Dorn ..................... G16H 40/63 715/810 |
| 2010/0249506 | A1 | 9/2010 | Prisco |
| 2013/0023730 | A1 | 1/2013 | Kitamura et al. |
| 2014/0005555 | A1 | 1/2014 | Tesar |
| 2014/0051922 | A1 | 2/2014 | Guthart et al. |

* cited by examiner

NAVIGATION ASSISTANCE SYSTEM FOR MEDICAL INSTRUMENTS

CROSS REFERENCE TO RELATED APPLICATIONS

This application is the U.S. National Stage of International Application Number PCT/EP2015/058107 filed on Apr. 14, 2015, which application claims priority under 35 USC § 119 to German Patent Application No. 10 2014 207 274.3 filed on Apr. 15, 2014. Both applications are hereby incorporated by reference in their entirety.

TECHNICAL FIELD

The present invention relates to navigation support systems for medical instruments, comprising a signal processing unit which has an input for real-time video image signals from an optical instrument, an input for instrument position signals, and access to tomography image data, and an output for outputting image signals, wherein the signal processing unit is designed to generate the output image signals from the real-time video image signals, the instrument position signals, and the tomography image data. The present invention also relates to a method for operating a navigation support system.

BACKGROUND OF THE INVENTION

Navigation support systems of the type mentioned at the outset serve to support invasive surgical interventions by means of visualization and are basically known from prior art. Real-time video image signals may, for example, originate from an endoscope or microscope as an optical instrument. Instrument position signals may be provided by an optical or electromagnetic position detection system for detecting the location and orientation of medical instruments, e.g. pointers, endoscopes or surgical instruments. Tomography image data are typically prepared preoperatively and stored in an image database of the navigation support system.

SUMMARY OF THE INVENTION

The invention is based on the task of providing a navigation support system for medical instruments which allows improved support for invasive surgical interventions.

According to the invention the task is solved by a navigation support system whose signal processing unit is further designed to generate the output image signals such that the real-time video image signals are permanently displayed centrally on an image display unit connected to the navigation support system in a round or oval central image display of an overall image, wherein the central image display extends at least in more than one half of the overall image in one direction of extension over the major part, but at least more than half of the overall image. At the same time, the signal processing unit is designed to generate the output signals in such a way that secondary images generated from tomography image data are partially superimposed or adjacent to the central image display in dependence on the instrument position signals.

The invention includes the knowledge that navigation support systems of the prior art so far only inadequately support the work of a surgeon in invasive surgical interventions, or even distract him. For example, navigation support systems of the prior art are designed for initially outputting, for example, an endoscopic, real-time video image signal on an image display unit and subsequently switching over to a common visualization of real-time video image signals, instrument position signals and tomography image data in the form of an image display unit divided into typically four sectors. In addition to the switching effect, this results in a disadvantageous presentation of the real-time video image signals due to a reduced size. Typically, an additional image display unit is provided for displaying the real-time video image signals. Thus, a second output for outputting image signals must also be provided at the navigation support system, which is a circuit engineering effort. On the other hand, in the case of an additional image display unit, the surgeon cannot easily simultaneously monitor both the first and second image display unit. These disadvantages are avoided by the inventive navigation support systems.

According to the invention, the signal processing unit is designed to generate the output image signals in such a way that the real-time video image signals are permanently displayed centrally and at the greatest possible imaging scale on an image display unit connected to the navigation support system in a round or oval central image display of an overall image, so that a surgeon does not need to look away from the central area of the image display unit during surgery.

Because the signal processing unit is further designed to generate the output image signals in such a way that secondary images generated from tomography image data are partially superimposed or adjacent to the central image display in dependence on the instrument position signals, the overall image is appropriately optimally utilized in each operating situation. A representation of secondary images adjacent to the central image display maybe sufficient, for example, if a surgical instrument is not yet in an operative target region. If a surgical instrument is already in or in close proximity to an operative target region, an enlarged or even the central image display overlapping representation of secondary images is desirable, since now the surgical instrument has to be guided even more precisely.

The invention thereby includes the knowledge that the surgeon typically guides the surgical instrument more slowly when positioned in or near an operative target region, or even remains in a position longer than outside an operative target region, and that a position and/or velocity information of the surgical instrument can be evaluated for the appropriate representation of secondary images. Correspondingly, the signal processing unit may be designed to evaluate instrument position signals and, as a function thereof, to generate the output image signals in such a way that the image display generated from tomography image data is adjacent to or partially superimposed on the central image display.

Advantageously, the inventive navigation support system results in the technical effect that a navigation support system requires only one output for outputting image signals with simultaneous distraction-free visualization of medical data because the visualization is based on instrument position signals.

In a preferred embodiment, the signal processing unit is designed to generate the output image signals such that the overall image extends over the entire area of the image display unit. The signal processing unit can be designed to generate the output image signals such that the central image display extends over more than half of the overall image in the vertical direction of extension. The signal processing unit may be designed to generate the output image signals such that the central image display extends over more than 60% of the overall preferably over more than 80%, and particularly more than 90% of the overall image, in a vertical direction of extension relative to an image display unit in the horizontal format (landscape). Accordingly, in the case of an image display unit in vertical format (portrait), a horizontal direction of extension is referred to.

Alternatively or additionally, the signal processing unit can be designed to generate the output image signals such that the central image display extends over more than half of the overall image in the horizontal direction of extension. It has been found to be advantageous if the signal processing unit is designed to generate the output image signals such that the overall image is displayed in widescreen format, in particular in the format 16:9. In this way, the surgeon is provided with an optimal field of view.

Preferably, the signal processing unit is designed to generate the cutout image signals such that axial, sagittal and coronary layers and/or sections, particularly of preoperatively recorded tomography image data, may be output to an image display unit as secondary images. For this purpose, the signal processing unit may be designed to read out tomography image data from an image database and to provide it correspondingly at its output for outputting image signals. Advantageously, the signal processing unit is designed to generate the output image signals such that the secondary image adjacent to the lower left corner of the overall image shows an axial section of a tomographic image, the secondary image adjacent to the upper left corner of the overall image shoves a sagittal section of a tomographic image and the upper right corner of the overall image shows a coronal section of a tomographic image. Preferably, the signal processing unit is designed to generate the output image signals in such a way that the secondary images and/or an auxiliary image and the central image display are represented in the sense of a densest circle package on the overall image, in particular when the secondary images do not overlap the central image display.

It has been found to be advantageous, if the signal processing unit is further designed to generate the output image signals such that an auxiliary image is adjacent to or partially superimposed over the central image display. The auxiliary image may display coordinates, notes, representations generated from tomographic data, or the like. The signal processing unit may be designed to generate the output image signals such that one or a plurality of secondary images and/or the auxiliary image are arranged axially to an operating point of the surgical instrument displayed in the central image display.

In a particularly advantageous embodiment, the signal processing unit is designed to generate the output image signals in such a way that the secondary images are only displayed when the navigation support system is in a navigation mode, i.e., particularly when a surgical instrument connected to the navigation support system is actually navigated. Otherwise, for example in a preparatory mode in which, for example, only an endoscope is inserted but no surgical instrument is navigated, the signal processing unit may be designed to generate the output image signals in such a way that the secondary images are blanked out. Advantageously, the secondary images are masked in order to not distract a surgeon. Switching between a navigation mode and a preparatory mode may take place, for example, at the push of a button or automatically as soon as a surgeon takes up or lays down the instrument to be navigated. For this purpose, for example, an instrument position signal may be used.

In order to react, adequately to intraoperative events, it has been found to be advantageous, if the signal processing unit is designed to generate the output image signals in such a way that the position of the secondary images in the overall picture is variable. Thus, one or a plurality of secondary images with particularly important contents may be moved closer to the attention focus of the surgeon. Particularly, one or a plurality of secondary images in the area of the central image display may be displayed upon user action. A user action may be, for example, a temporal persistence with the instrument or a defined movement of the instrument.

Also, if the content of a secondary image is important, it may be necessary to display this at a magnified scale. Accordingly, the signal processing unit may be designed in such a way that one or a plurality of secondary images are displayed magnified. The position and/or the size of one or a plurality of secondary images may also be variable in such a way that the central image display is overlapped. Alternatively, the position and/or the size of one or more secondary images may be fixed in the overall image. In order to enable an additionally improved visualization, the signal processing unit may be designed in such a way that when secondary images are displayed overlapping in the region of the central image display, this is done in such a way that no target structures and/or images of an instrument are masked.

It has been found to be advantageous if the signal processing unit is designed to recognize a signal component of the real-time video image signals representing an instrument in use. The signal processing may recognize an instrument on an endoscopic and/or microscopic real-time video image signal particularly by means of pattern recognition and/or display the instrument in a schematic representation on an image display unit. The signal processing unit may also be designed to recognize tissue structures.

It has been found to be advantageous if the signal processing unit is designed to generate the output image signals such that a signal component of the real-time video image signals representing a recorded instrument is highlighted visually when the instrument approaches a critical structure and/or target structure, particularly when approaching a pre-determinable position.

According to the invention, the task is also solved by a method for operating a navigation support system described above, comprising the step of:

Generating output image signals from real time video image signals, instrument position signals and tomography image data such that the real-time video image signals are permanently displayed centrally on an image display unit connected to the navigation support system in a round or oval central image field of an overall image, wherein the overall image extends in at least one direction of extension across more than half of the overall image, wherein secondary images generated from tomography image data are adjacent to or partially superimposed over the central image display in dependence on the instrument position signals.

The inventive method may comprise process steps which correspond to the device features explained with regard to the navigation support system—and vice versa. If the signal processing unit, for example, with respect to the navigation support system, is designed to generate the output image signals in such a way that the overall image is displayed in widescreen format, particularly in the format 16:9, the method step is also disclosed: Generating the output image signals by the signal processing unit such that the overall image is displayed in widescreen format, particularly in the format 16:9.

BRIEF DESCRIPTION OF THE DRAWINGS

Embodiments of the invention are now described below with reference to the drawings. Additional advantages, features and details of the invention will become apparent from the following description of the preferred embodiments as well as from the drawings showing in.

DETAILED DESCRIPTION

Figure 1:
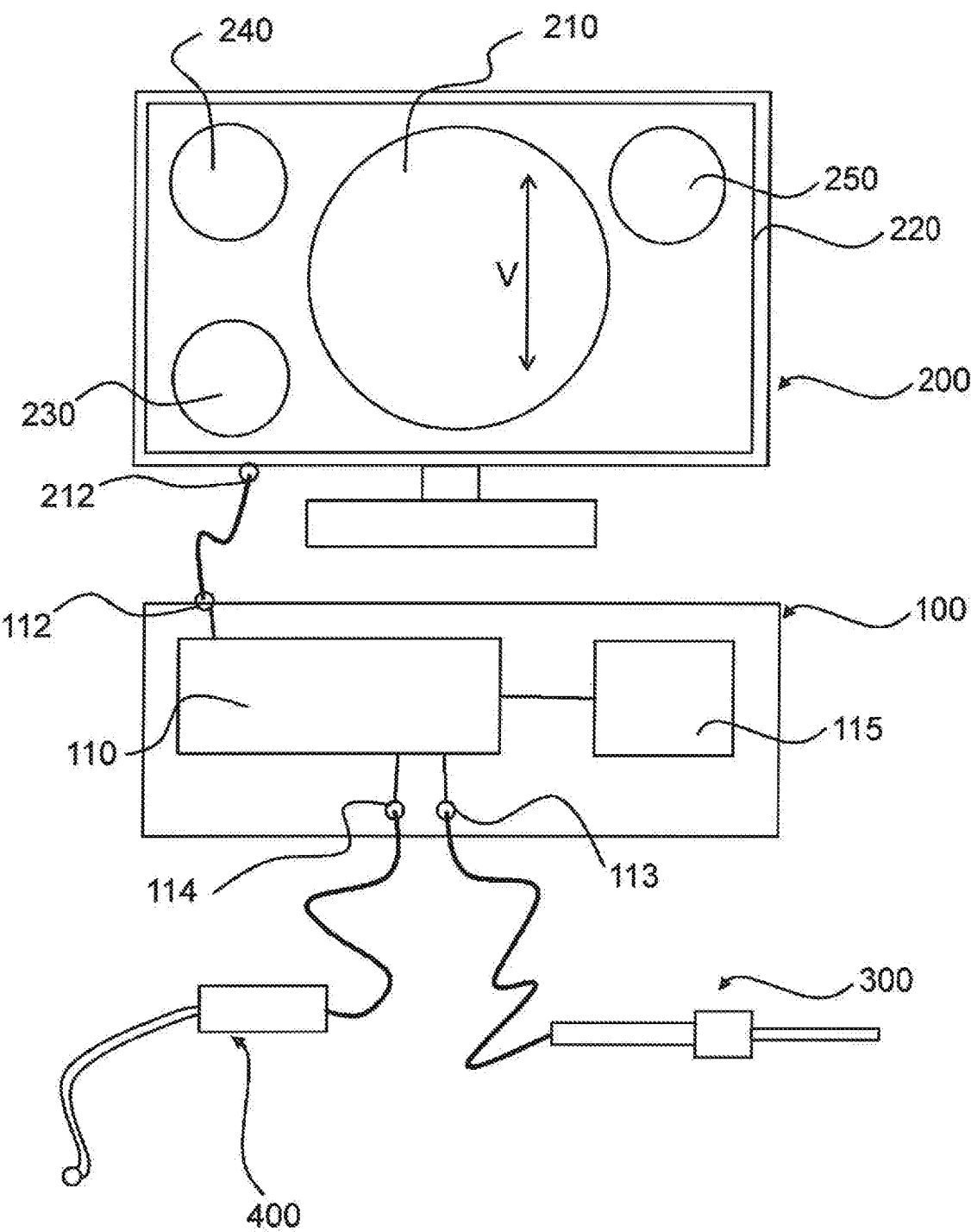
FIG. 1 a schematic representation of an inventive navigation support system, which is connected to an image display unit, and two instruments.

FIG. 1 shows a navigation support system 100, an image display unit 200, a surgical instrument 300 configured as a pointer, optical instrument 400 configured as an endoscope. The navigation support system 100 has a signal processing unit 110 which in turn has an input 114 for real-time video image signals from the optical instrument 400, an input 113 for instrument position signals, as well as access to tomography image data 115, and an output 112 for outputting image signals. The optical instrument 400 is connected to the input 114 for real-time video image signals and the surgical instrument 300 is connected to the input 113 for instrument position signals. The image display unit 200 is connected to the output 112 for outputting image signals. The signal processing unit 110 is designed to generate output image signals from the real-time video image signals, the instrument position signals and the tomography image data 115. These output image signals are displayed on the image display unit 200 in the form of an overall image 220 having an image format of 16:9. The overall image 220 extends across the entire area of the image display unit 200.

As shown in FIG. 1, the signal processing unit 10 is configured to generate the output image signals and to indicate on the image display unit 200 that the real-time video image signals are displayed permanently centrally in a round central image display 210 of the overall image 220. It is shown that the central image display 210 extends in the vertical extension direction V across more than half or the overall image 220. In addition to the central image, display 210, secondary images 230, 240, 250 generated from tomography image data are instrument position signals which do not overlap the central image display 220 in the present case. The secondary image 230 adjacent to the lower left corner of the overall image 220 shows an axial section of a tomography image, the secondary image 240 adjacent to the upper left corner of the overall image 220 shows a sagittal section of a tomography image and the secondary image 250 adjacent to the upper right corner of the overall image 220 shows a coronal section of a tomography image. In other words, the signal processing unit 110 is designed to generate the output image signals such that an axial section is shown in the lower left corner of the overall image 220, a sagittal section in the upper left corner, and a coronal section of a tomography image in the upper right corner of the overall image. The central image display 210 and the secondary images 230, 240, 250 have a fixed dimension and position on the overall image 220. For the sake of simplicity, the actual image contents of the respective sections are not shown here.

Figure 2:
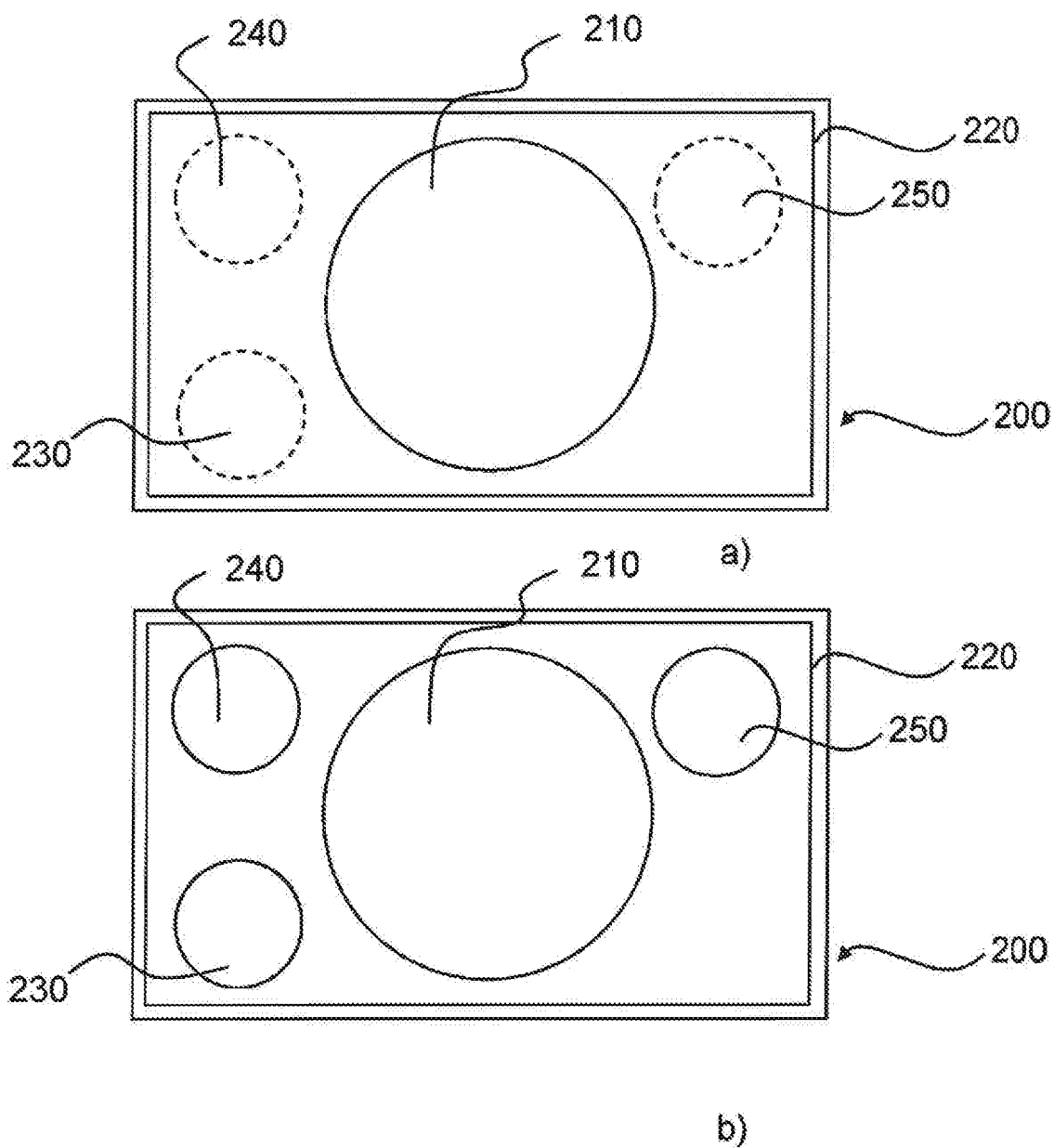
FIG. 2 a schematic representation of an image display with three secondary images.

FIG. 2 also shows an image display unit 200 with an overall image 220. Both in FIG. 2a) and in FIG. 2b), real-time video image signals of the optical instrument (not shown) are displayed permanently centrally in around central image field 210 of the overall image 220. As also in the other figures, during operation, a permanent representation is represented by a solid contour. FIG. 2a) now shows a preparation mode in which the secondary images 230, 240, 250 are masked in order not to disturb the surgeon when introducing an optical instrument (not shown). The signal processing unit (not shown) thus generates the output image signals such that the secondary images 230, 240, 250 are not displayed or are masked. FIG. 2b) again shows a navigation mode in which the signal processing unit (not shown) generates the output image signals in such a way that the secondary images 230, 240, 250 are displayed or not masked. As also in the other figures, during operation, a masking is represented by a dashed outline.

Figure 3:
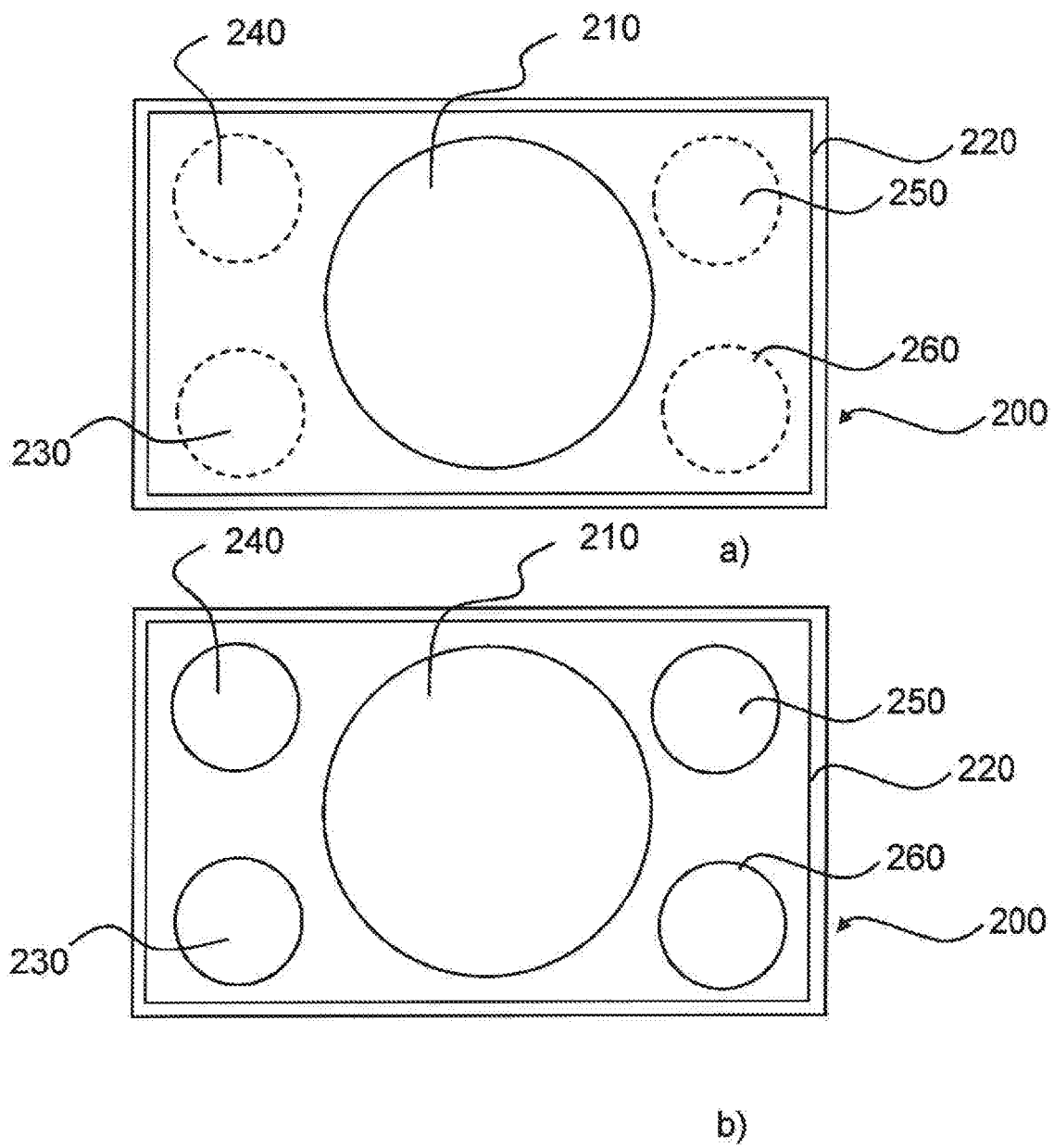
FIG. 3 a schematic representation of an image display with three secondary images and an auxiliary image.

FIG. 3 also shows an image display unit 200 with an overall image 220. Both in FIG. 3a) and in FIG. 3b), real-time video image signals of the optical instrument (not shown) are displayed permanently centrally in a round central image field 210 of the overall image 220. FIG. 3b) shows a navigation mode in which the signal processing unit (not shown) generates the output image signals such that the secondary images 230, 240, 250 are displayed or not masked. In addition, the signal processing unit (not shown) generates the output image signals such that an auxiliary image 260 generated from tomographic data is displayed closest to the lower right corner of the overall image 220. In the preparation mode, shown in FIG. 3a), both the secondary images 230, 240, 250 and the auxiliary image 260 are masked. The signal processing unit (not shown) thus generates the output image signals such that the secondary images 230, 240, 250 and auxiliary image 260 are not displayed or masked. The central image display 210, the secondary images 230, 240, 250 and the auxiliary image 260 have a fixed dimension and position on the overall image 220.

Figure 4:
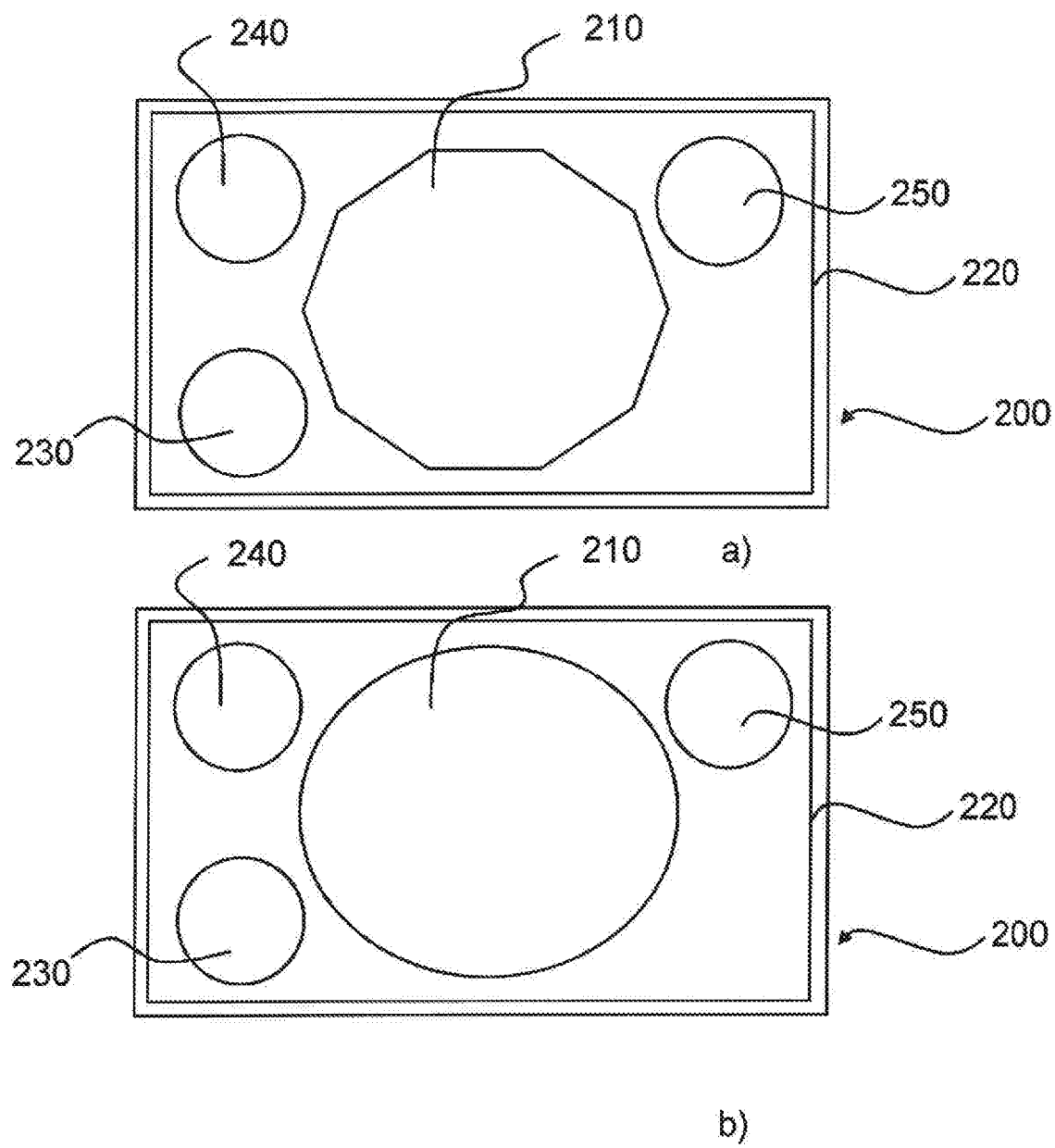
FIG. 4 a schematic representation of two additional image displays.

FIG. 4 also shows an image display unit 200 with an overall image 220. In FIG. 4a), real-time video image signals of the optical instrument (not shown) are displayed permanently centrally in a substantially round central image display 210 of the overall image 220. In FIG. 4b), real-time video image signals of the optical instrument (not shown) are displayed permanently centrally in an oval central image display 210 of the overall image 220. In both subfigures it is shown that the central image display 210 extends in the vertical extension direction V across more than half of the overall image 220.

Figure 5:
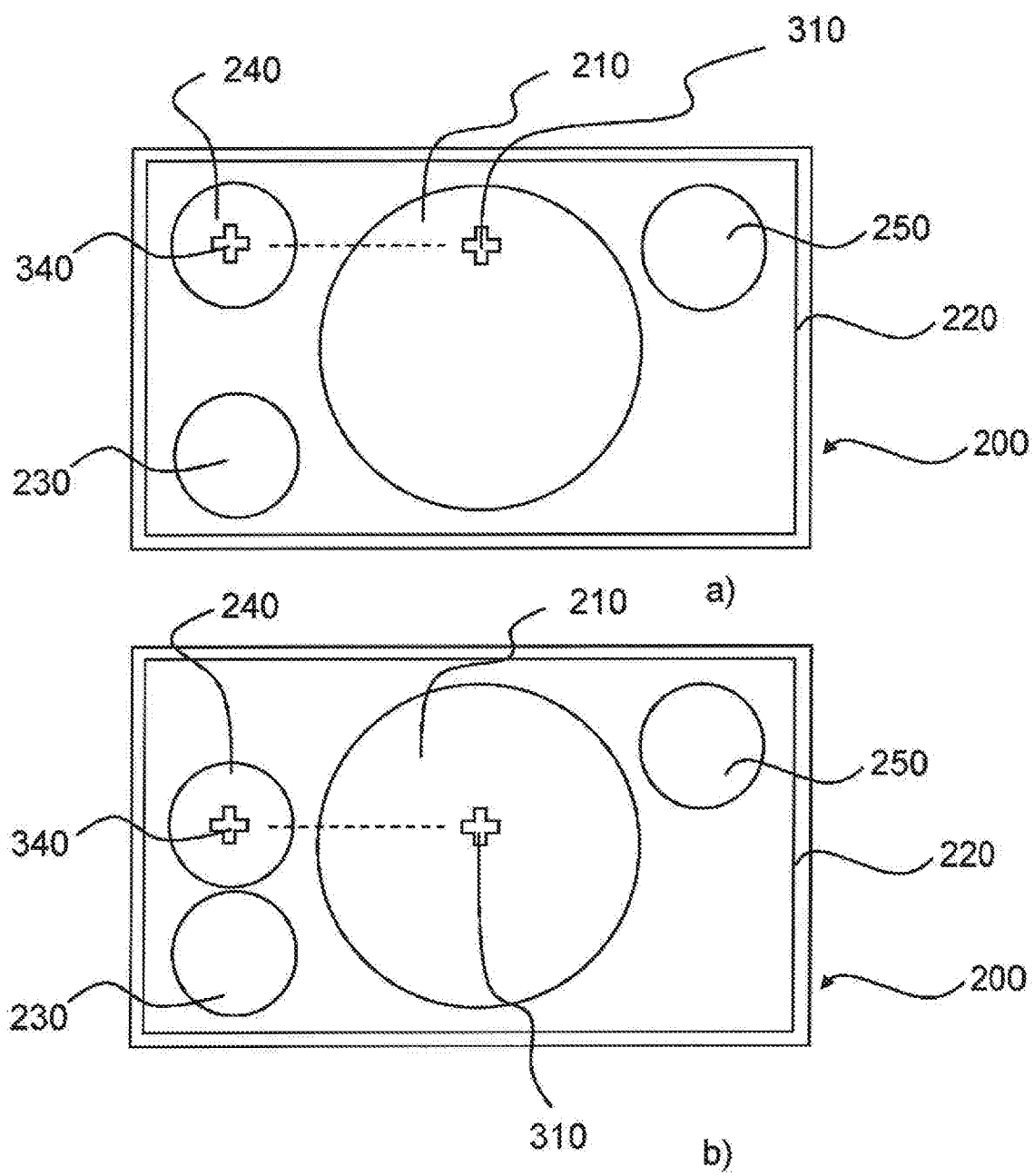
FIG. 5 a schematic representation of an image display with an operating point of a surgical instrument.

A navigation support system whose signal processing unit (not shown) generates the output image signals such that the position of the secondary images 230, 240, 250 in the overall image 220 is variable, is shown in FIG. 5. The representation of the overall image 220 in FIG. 5a) corresponds to that in FIG. 1 and in FIG. 2b) with the difference that in FIG. 5a) in the central frame 210 a central reticle 310 and a sagittal reticle 340 is shown in the sagittal secondary image 240, wherein the reticles 310, 340 respectively represent the operating point of the surgical instrument 300 (not shown). The dashed line indicates that the central reticle 310 and the sagittal reticle 340 are displayed by the navigation support system horizontally on the same axis on the overall image 220. If the surgical instrument 300 (not shown) is then moved into a different position, as shown in FIG. 5b), the central reticle 310 is displaced on the fixed central image display 210, in the present case downwards. Since a common horizontal position of the central reticule 310 and the sagittal reticle 340 is desired in the embodiment of FIG. 5—offering the surgeon a more intuitive image display—the signal processing unit (not shown) generates the output image signals such that the position of the sagittal secondary image 240 is displaced with respect to its initial position, so that the sagittal reticle 340 again reaches a common horizontal axis with the central reticle 310. In the embodiment of FIG. 5, only the sagittal secondary image 240 is shown as variable in position. Of course, the axial secondary image 230 and/or the coronal secondary image 250 may also be variable in position correspondingly.

Figure 6:
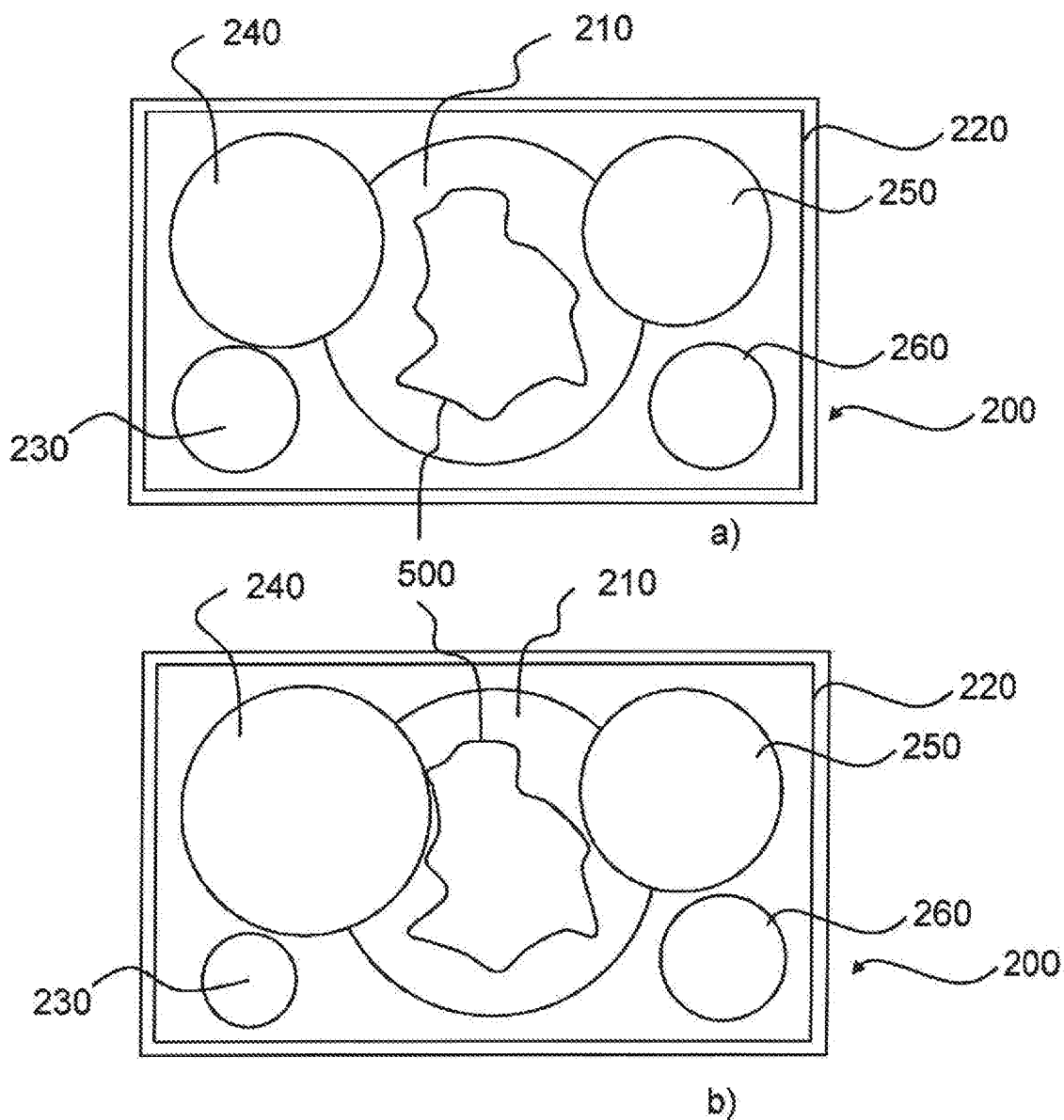
FIG. 6 a schematic representation of an image display with three secondary images and an auxiliary image, wherein two secondary images are magnified and overlapping the central image display.

An additional embodiment is shown in FIG. 6. FIG. 6 also shows an image display unit 200 with an overall image 220. Both in FIG. 6a) and in FIG. 6b), real-time video image signals of the optical instrument (not shown) are displayed permanently centrally in a round central image field 210 of the overall image 220. In contrast to the above-described embodiments, the sagittal secondary image 240 and the coronal secondary image 250 are indicated in the region of the central image display 220. In particular, the sagittal secondary image 240 and the coronal secondary image 250 are enlarged and overlap the central image display 220. On the other hand, the axial secondary image 230 and the auxiliary image are displayed outside the central image display 220 and do not overlap. A magnification of the sagittal secondary image 240 and of the coronal secondary image 250 was effected in the present case such that the signal processing unit 110 is designed to evaluate instrument position signals and to generate the output image signals in a magnified manner as a function thereof. In the present case, the surgeon has approached the target structure 500 with the instrument 300 and remains briefly in this position (first user action). FIG. 6a) shows the overall image 220 after a first user action, FIG. 6b) after a second user action, for example an additional approach to the target structure 500.

A target structure 500 of an instrument 300 (not shown) is shown on the central image display 210, i.e., for example, an operation area which must constantly be visible on the central image display 210 during surgery, i.e., it must not be concealed or masked. Both in FIG. 6a) and in FIG. 6b), the secondary images 230, 240, 250 and the auxiliary image are displayed such that the target structure 500 is not concealed. However, part of the central image display 210 is concealed. In the embodiment of FIG. 6, the signal processing unit 110 (not shown) is configured to recognize the signal components of the real-time video image signals representing the target structure 500 and, by means of a plausibility check, to prevent the secondary images 230, 240, 250 and the auxiliary image 260 from being displayed by a user action in a magnified fashion, so that the target structure 500 is concealed in the central image display 210. Starting from FIG. 6a), it is possible through a user action, to further magnify the display of the secondary images 230, 240, 250 and the auxiliary image 260, since the target structure 500 is not concealed yet in the central image display 210 by some distance. FIG. 6b) shows the situation after such a user action. Starting from FIG. 6b), it would be impossible to further magnify the sagittal image 240 and the coronary secondary image 250 by a user action, since otherwise the target structure 500 would be concealed in the central image display 210.

Figure 7:
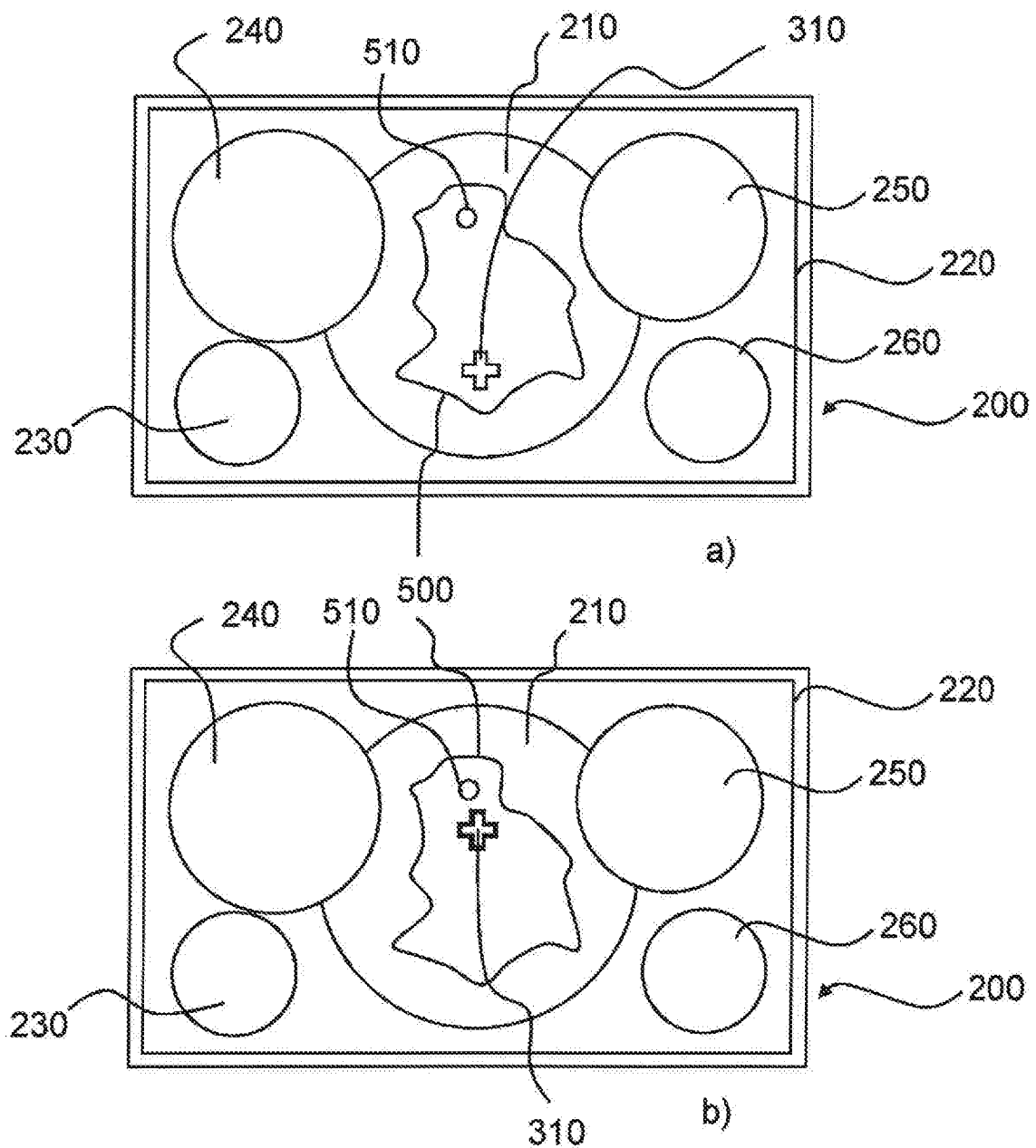
FIG. 7 a schematic representation of an image display with a highlighted operating point of a surgical instrument.

Finally, FIG. 7 shows an embodiment in which signal components of the real-time video image signals representing a recorded instrument are recognized. For this purpose, the signal processing unit 110 (not shown) is configured to perform a pattern recognition in the real-time video image signal, and thus to display the recognized instrument or its working point as a central reticle 310. Thus, the instrument 300 (not shown) is represented in the central image display 210 by the central reticle 310. When the instrument 300 approaches the pre-determinable position 510, the central reticle 310 is optically highlighted. In FIG. 7a), a central reticle 310 is clearly spaced from the pre-determinable position 510, i.e. the instrument 300 (not shown) is also distant in the operating region from the pre-determinable position 510, for example, at a location where an incision is to be made. Thus, the central reticle 310 is shown in the central image display 210 in normal line thickness. If the instrument 300 (not shown) is now brought into the vicinity of the pre-determinable position 510, the central reticle 310 is shown in the central image display 210 in the vicinity of the pre-determinable position 510 as well as the reticle 310 is shown in the central image display 210 in thicker line thickness.

Figure 8:
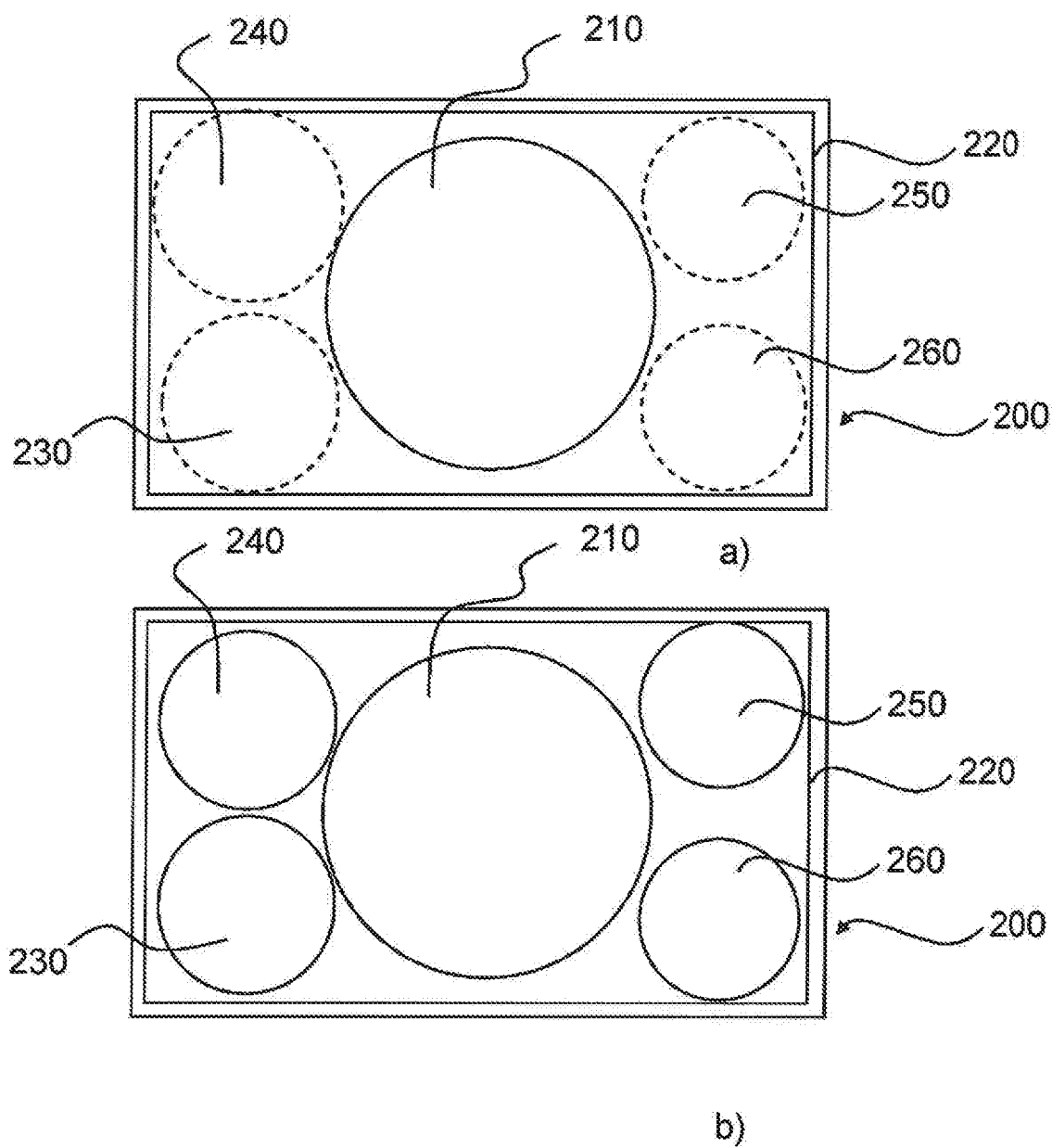
FIG. 8 a schematic representation of an image display with three secondary images and auxiliary image arranged according to a densest cross package.

FIG. 8 shows a schematic representation of an image display with three secondary images and an auxiliary image arranged according to a densest circle package. The signal processing unit 110 is configured to generate the output image signals such that an axial section is shown in the lower left corner of the overall image 220, a sagittal section in the upper left corner and a corona section of a tomography image in the upper right corner of the overall image; in the right lower corner of the overall image, an auxiliary image 260 is shown. The central image display 210 and the secondary images 230, 240, 250 and the auxiliary image 260 have a fixed extension and position in the overall image 220. The signal processing unit 110 is configured to generate the output image signals in such a way that the secondary images 230, 240, 250, the auxiliary image 260 and the central image display 210 are shown according to a densest circle package in the overall image 220. The secondary images 230, 240, 250, the auxiliary image 260, and the central image display 210 do not overlap each other.

LIST OF REFERENCE NUMBERS

100 Navigation support system
110 Signal processing unit
112 Output
113, 114 Input
115 Tomography image data
200 Image display unit
210 Image display
220 Overall image
230, 240, 250 Secondary images
260 Auxiliary image
300 Surgical instrument
310, 340 Reticle
400 Optical instrument
500 Target structure
510 Position
V Vertical direction of extension

What is claimed is:

1. A navigation support system for detecting a location of a medical instrument relative to a patient and illustrating the location of the medical instrument in an image of a surgical area on an image display unit, wherein said navigation support system comprises: an optical instrument for providing real-time video image signals, a position detection system that is configured for detecting location and orientation of the medical instrument and for providing instrument position signals that represent location and orientation of this medical instrument, a signal processing unit having an input for real-time video image signals from said optical instrument, an input for instrument position signals that represent location and orientation of the medical instrument and access to tomography image data that are stored in an image database of the navigation support system, and an output for outputting image signals, an image display unit for displaying an overall image, wherein the image display unit is connected to the output of said signal processing unit, wherein the signal processing unit is configured to generate output image signals from the real-time video image signals, the instrument position signals and the tomography image data, and wherein the signal processing unit is further configured to generate the output image signals such that in the overall image that is displayed on the image display unit, the real-time video image signals are displayed permanently centrally on said image display unit in a round or oval central image field of said overall image, wherein the central image field extends at least in one direction of extension across more than half of said overall image, and secondary images generated from tomography image data are displayed automatically adjacent to or partially superimposed over said central image field in dependence on a detected location and orientation of the medical instrument represented by said instrument position signals.

2. The navigation support system according to claim 1, wherein the signal processing unit is further configured to generate the output image signals such that the overall image extends across the entire area of the image display unit.

3. The navigation support system according to claim 1, wherein the signal processing unit is further configured to generate the output image signals such that the central image field extends in the vertical direction of extension across more than half of the overall image.

4. The navigation support system, according to claim 1, wherein the signal processing unit is configured to generate the output image signals such that the overall image is displayed in widescreen format.

5. The navigation support system according to claim 1, wherein the signal processing unit is further configured to generate the output image signals such that the secondary images are axial, sagittal and coronary layers and/or sections.

6. The navigation support system according to claim 1, wherein the signal processing unit is further configured to generate the output image signals such that the secondary images are only shown in a navigation mode and are otherwise particularly masked.

7. The navigation support system according to claim 1, wherein the signal processing unit is further configured to generate the output image signals such that the positions of the secondary images in the overall image are variable.

8. The navigation support system according to claim 1, wherein the signal processing unit is further configured to generate the output image signals such that the secondary images are only shown in the area of the central image field upon user action.

9. The navigation support system according to claim 1, wherein the signal processing unit is further configured to generate the output image signals such that when secondary images are displayed in the region of the central image field or overlapping it, this is done in such a way that no target structures/images of an instrument are concealed.

10. The navigation support system according to claim 1, wherein the signal processing unit is configured to recognize signal components of the real-time video image signals representing an instrument in use.

11. The navigation support system according to claim 1, wherein the signal processing unit is configured to generate the output image signals such that a signal component of the real-time video image signals representing an instrument in use is highlighted visually when the instrument approaches a critical structure and/or target structure, particularly when approaching a pre-determinable position.

12. A method for operation a navigation support system according to claim 1, comprising:
  generating output image signals from real-time video image signals, instrument position signals and tomography image data such that the real-time video image signals are permanently displayed centrally on an image display unit connected to the navigation support system in a round or oval central image field of an overall image, and wherein the overall image extends in at least one direction of extension across more than half of the overall image, wherein secondary images generated from tomography image data are adjacent to or partially superimposed over the central image field in dependence on the instrument position signals.

* * * * *